US010512568B2

(12) United States Patent
Carney et al.

(10) Patent No.: US 10,512,568 B2
(45) Date of Patent: Dec. 24, 2019

(54) WEARABLE ABSORBENT HYGIENE ARTICLE COMPRISING AN ELECTRONICS UNIT

(71) Applicant: SCA Hygiene Products AB, Göteborg (SE)

(72) Inventors: Joshua Carney, Göteborg (SE); Yossef Schvetz, Milan (IT); Serdar Ozsumer, Milan (IT); Manuel Tramontana, Milan (IT); Alessandro Locati, Milan (IT)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 15/775,075

(22) PCT Filed: Nov. 13, 2015

(86) PCT No.: PCT/EP2015/076573
§ 371 (c)(1),
(2) Date: May 10, 2018

(87) PCT Pub. No.: WO2017/080620
PCT Pub. Date: May 18, 2017

(65) Prior Publication Data
US 2018/0353355 A1     Dec. 13, 2018

(51) Int. Cl.
*A61F 13/42* (2006.01)
*A61F 13/84* (2006.01)
*H01H 36/00* (2006.01)

(52) U.S. Cl.
CPC .............. *A61F 13/84* (2013.01); *A61F 13/42* (2013.01); *H01H 36/0006* (2013.01);
(Continued)

(58) Field of Classification Search
CPC .... A61F 13/42; A61F 13/55115; A61F 13/84; A61F 2013/424; A61F 2013/8479;
(Continued)

(56) References Cited

U.S. PATENT DOCUMENTS 3,341,676 A * 9/1967 Schwarz .............. H01H 29/004
  200/211
3,769,497 A * 10/1973 Frank .................. A61M 1/0021
  235/94 R
(Continued)

FOREIGN PATENT DOCUMENTS

JP   S53-085958   7/1978
RU   2316300 C2   2/2008
RU   2553008 C2   6/2015

OTHER PUBLICATIONS

European Office Action dated Mar. 4, 2019 issued in European patent application No. 15 795 152.6.
(Continued)

*Primary Examiner* — Susan S Su
(74) *Attorney, Agent, or Firm* — Drinker Biddle & Reath LLP

(57) ABSTRACT

A wearable absorbent hygiene article includes a liquid permeable top layer, a back layer, an absorbent member, an electronics unit, a power source and a switch. The liquid permeable top layer is adapted to face the wearer during use. The back layer is opposite to the top layer. The absorbent member is located between the top layer and the back layer. The switch operably couples the electronics unit to the power source. The switch is configured such that the power source supplies power to the electronics unit when the switch is in an ON state and such that the power source does not supply power to the electronics unit when the switch is
(Continued)

in an OFF state. The power source, the switch and at least a portion of the electronics unit are disposed between the top layer and the back layer.

21 Claims, 15 Drawing Sheets

(52) U.S. Cl.
CPC . *A61F 2013/424* (2013.01); *A61F 2013/8479* (2013.01); *A61F 2013/8488* (2013.01)

(58) Field of Classification Search
CPC ........ A61F 2013/8488; H01H 36/0006; H01H 36/0013; H01H 36/002; H01H 36/0026
See application file for complete search history.

(56) References Cited

U.S. PATENT DOCUMENTS

| | | | |
|---|---|---|---|
| 6,477,410 B1* | 11/2002 | Henley | A61N 1/0428 601/1 |
| 2004/0019400 A1 | 1/2004 | Popp et al. | |
| 2004/0113801 A1 | 6/2004 | Gustafson et al. | |
| 2004/0178807 A1* | 9/2004 | Sahlberg | A61F 13/42 324/694 |
| 2005/0033250 A1* | 2/2005 | Collette | A61F 13/42 604/361 |
| 2006/0266104 A1 | 11/2006 | Gordon | |
| 2007/0252711 A1* | 11/2007 | Long | A61F 13/42 340/573.5 |
| 2008/0033383 A1* | 2/2008 | Cantor | A61F 13/42 604/361 |
| 2009/0163111 A1* | 6/2009 | Garbos | A63H 3/28 446/298 |
| 2010/0056963 A1 | 3/2010 | Shaviv | |
| 2011/0095884 A1* | 4/2011 | Xu | A61F 13/42 340/539.11 |
| 2011/0140885 A1* | 6/2011 | Hummer | G08B 21/12 340/539.13 |
| 2011/0140903 A1 | 6/2011 | Collins et al. | |
| 2012/0172824 A1 | 7/2012 | Khaknazarov et al. | |
| 2015/0320609 A1 | 11/2015 | Thoen | |
| 2016/0250081 A1* | 9/2016 | Pugh | G08B 21/245 604/361 |
| 2018/0369031 A1 | 12/2018 | Carney et al. | |

OTHER PUBLICATIONS

Russian Office Action dated Jan. 10, 2019 issued in Russian patent application No. 2018121031(6 pages) and its partial English-language translation thereof (2 pages).
"Types of Magnet," https://www.thomasnet.com/articles/electrical-power-generation/magnet-types, printed May 10, 2019.
Office Action dated May 15, 2019 issued in U.S. Appl. No. 15/775,195 with double-patenting rejection on p. 3.
Decision to Grant dated Jun. 11, 2019 issued in Russian patent application No. 2018121031 (11 pages) and its English-language translation thereof (6 pages).
Decision to Grant dated Jun. 11, 2019 issued in Russian patent application No. 2018121039 (13 pages) and its English-language translation thereof (8 pages).
Japanese Office Action dated Aug. 9, 2019 issued in Japanese patent application No. 2018-524360 (5 pages) and its English-language translation thereof (5 pages).
Japanese Office Action dated Aug. 9, 2019 issued in Japanese patent application No. 2018-524365 (4 pages) and its English-language translation thereof (5 pages).

* cited by examiner

WEARABLE ABSORBENT HYGIENE ARTICLE COMPRISING AN ELECTRONICS UNIT

CROSS-REFERENCE TO PRIOR APPLICATION

This application is a § 371 National Stage Application of PCT International Application No. PCT/EP2015/076573 filed Nov. 13, 2015, which is incorporated herein in its entirety.

TECHNICAL FIELD

The present disclosure relates to a wearable absorbent hygiene article, and particularly to a wearable absorbent hygiene article with an electronics unit, a power source and a switch. The present disclosure also relates to methods of using the wearable absorbent hygiene article.

BACKGROUND

Typically, a separate external attachable logging unit may be used to monitor the conditions of a wearable absorbent hygiene article. An example logging unit may include an electronics unit and a power source such as a cell. The electronics unit may include sensors which monitor, and optionally transmit, the conditions of the wearable absorbent hygiene article such as the wetness. Such electronics units may include a wetness sensor and/or a transmitter and/or a receiver. The electronics unit may be powered by the power source. Typically, the wearable absorbent hygiene article is sold and packaged separately from the logging unit, and, therefore, the user must attach the logging unit to the wearable absorbent hygiene article before using the wearable absorbent hygiene article. The logging unit is typically attachable to the outside surface of the wearable absorbent hygiene article. Furthermore, the logging unit may be of a substantial size.

However, with such systems, use of the system typically includes additional complicated steps in addition to the steps required to use a conventional wearable absorbent hygiene article.

In view of the above, there is a need for a convenient-to-use wearable absorbent hygiene article with electronic capabilities. There is also a need for improved methods of using the wearable absorbent hygiene article.

SUMMARY

It is desired to provide a convenient-to-use wearable absorbent hygiene article with electronic capabilities. It is also desired to provide a method of using the wearable absorbent hygiene article.

According to a first aspect, there is provided a wearable absorbent hygiene article. The wearable absorbent hygiene article includes a liquid permeable top layer, a back layer, an absorbent member, an electronics unit, a power source and a switch. The liquid permeable top layer is adapted to face the wearer during use. The back layer is opposite to the top layer. The absorbent member is located between the top layer and the back layer. The switch operably couples the electronics unit to the power source. The switch is configured such that the power source supplies power to the electronics unit when the switch is in an ON state and such that the power source does not supply power to the electronics unit when the switch is in an OFF state. The power source, the switch and at least a portion of the electronics unit are disposed between the top layer and the back layer.

Throughout this disclosure, the term 'wearable absorbent hygiene article' is to be interpreted as any article that can be worn by a user and which may absorb certain substances expelled by the user. Wearable absorbent hygiene articles include pull-on diapers; refastenable diapers; reusable diapers; and other types of diapers.

The liquid permeable top layer may be adapted to allow a fluid such as urine or other bodily fluids to pass through. The back layer may be a liquid impermeable back layer adapted to prevent the fluid from passing through.

Throughout this disclosure, the term 'electronics unit' refers to any unit which includes electronic components and which requires electrical power to perform its intended function.

Throughout this disclosure, the term 'power source' refers to any device which is capable of storing energy for a period of time. The power source may supply electrical power.

When the switch is in an ON state, the power source supplies power to the electronics unit such that the electronics unit may perform its intended function. When the switch is in an OFF state, the power source does not supply power to the electronics unit such that the electronics unit cannot perform its intended function. When the switch is in the OFF state, the power source largely maintains its stored energy.

It is envisaged that any sensors, parts of such sensors, or components connecting the sensors with other components of the electronics unit, may be disposed on an outer surface of the absorbent article, such as on the wearer-facing side of the top layer, or on the outer surface of the back layer. For example, chemical sensors such as gas sensors, may be positioned on the outer surface of the back layer to provide indications of faecal discharge event; biological sensors, such as for detecting the presence of bacteria in urine, may be positioned on the wearer-facing side of the top layer, which conducting leads, connecting such sensors to other components of the electronics unit may be disposed between the top layer and the back layer. Also, a wetness sensor may be disposed between the top layer and the back layer, while conducting leads, connecting such sensors to other components of the electronics unit may be disposed on the outer surface of the back layer. It is also envisaged that the complete electronics unit is disposed between the top layer and the back layer.

The top layer and the back layer may not be the only layers of the wearable absorbent hygiene article. Rather, further layers may be provided between the top layer and the back layer. Such further layers will be known to the person skilled in the art.

The absorbent member may be located anywhere between the top layer and the back layer.

With such configurations, attaching a separate logging unit to the wearable absorbent hygiene article is not required as the electronic capabilities are already embedded in the wearable absorbent hygiene article.

Hence, with such configurations, it is possible to provide a convenient-to-use wearable absorbent hygiene article with electronic capabilities.

In one embodiment, the electronics unit includes at least one sensor for sensing a physical environment present in the wearable absorbent hygiene article. In a particular embodiment, the at least one sensor is a wetness sensor and/or a temperature sensor and/or a chemical sensor and/or a biological sensor.

The wetness sensor may be configured to detect the presence and/or level of a liquid. The temperature sensor may be configured to detect the temperature present. The chemical sensor may be configured to detect one or more chemicals. The biological sensor may be configured to detect biological matter such as bacteria present in urine.

In one embodiment, the electronics unit includes a transmitter and/or a receiver.

In one embodiment, the power source is a cell, for example, a paper cell.

With such configurations, the power source may form a low profile which may reduce the comfort caused to the user.

In one embodiment, the wearable absorbent hygiene article includes a first panel region and a second panel region. The switch is further configured such that a movement of the first panel region relative to the second panel region switches the switch from the OFF state to the ON state.

Throughout this disclosure, the term 'panel region' refers to an area of a panel of the wearable absorbent hygiene article. Such 'panel regions' refer to the whole region of the panel including the corresponding regions of the top layer and the back layer.

As the electronics unit and the power source are included in the wearable absorbent hygiene article, the power source may start powering the electronics unit after manufacturing/packaging of the wearable absorbent hygiene article. Accordingly, the power source will power the electronics unit for the duration from the completion of manufacturing/packaging to just prior to use. During this time, the wearable absorbent hygiene article and the electronics unit are not being used, and, therefore, the energy in the power source is being wasted. Subsequently, when the wearable absorbent hygiene article is put to use, a large portion of the capacity of the power source may already be depleted, and, therefore, the electronics unit may have a limited period in which it may be powered by the power source. The duration in which the wearable absorbent hygiene article is not being used can vary considerably, and may range from a few months to a few years. During this time, the wearable absorbent hygiene article may be transported and stored for long periods of time. Depending on the size of the power source and when the wearable absorbent hygiene article is finally put to use, it may be that the power source does not have any stored energy remaining in it.

A user of such wearable absorbent hygiene articles may have to use many wearable absorbent hygiene articles over a period of time. Accordingly, it is desirable that the use of the wearable absorbent hygiene article does not involve any complicated steps and should ideally involve the same steps as the use of a typical wearable absorbent hygiene article—any additional steps in using a wearable absorbent hygiene article with an electronics unit may detract from the convenience of using the product.

With recent developments of low-cost, environmentally-friendly, low profile, disposable power sources and semiconductor chips, a wearable absorbent hygiene article may be provided with the power source and/or at least a portion of the electronics unit disposed between two layers of the wearable absorbent hygiene article. With such wearable absorbent hygiene articles, the power source and/or at least a portion of the electronics unit may be integrated within the wearable absorbent hygiene article such that access to the power source and/or the electronics unit is limited or not possible.

In view of the above, there is a need for an improved convenient-to-use wearable absorbent hygiene article in which an electronics unit may be powered for a longer period of time when the wearable absorbent hygiene article is in use.

Typically, during use of the wearable absorbent hygiene article, the article is unpackaged from a packaging; and/or unfolded from a folded configuration; and/or applied to a user. With the above configuration, in the unpacking/unfolding/applying steps a first panel region of the wearable absorbent hygiene article may be moved relative to a second panel region of the wearable absorbent hygiene article, thereby causing the switch to automatically switch from the OFF state to the ON state.

Hence, with such a configuration, it is possible to provide a convenient-to-use wearable absorbent hygiene article in which an electronics unit may be powered for a longer period of time when the wearable absorbent hygiene article is in use.

In one embodiment, the wearable absorbent hygiene article is in a folded configuration where the wearable absorbent hygiene article is folded such that the first panel region and the second panel region at least partially overlap.

Typically, in a folded configuration at least two areas of the wearable absorbent hygiene article will overlap. Accordingly, with such a configuration, upon unfolding the wearable absorbent hygiene article, which may be an essential step in the application of the wearable absorbent hygiene article, the switch would automatically switch from the OFF state to the ON state. This provides for a reliable switching.

In one embodiment, the wearable absorbent hygiene article includes a main portion. The first panel region is one region of the main portion. The second panel region is another region of the main portion.

With such a configuration, a movement of one region of the main portion relative to another region of the main portion may cause the switch to switch from the OFF state to the ON state. A movement of one region of the main portion relative to another region of the main portion typically occurs during unpacking/unfolding/application of the wearable absorbent hygiene article. Accordingly, with such a configuration, no extra steps are required to start powering the electronics unit. Hence, with such a configuration, the switch would automatically switch from the OFF state to the ON state during unpacking/unfolding/application of the wearable absorbent hygiene article. Moreover, typically, the main portion is the most padded area and, therefore, with such a configuration, the power source, electronics unit and switch do not cause substantial discomfort to the user. Also, as the electronics unit is typically provided for in the main region, such a configuration allows for a simple arrangement as the switch is disposed relatively close to the electronics unit.

In one embodiment, the wearable absorbent hygiene article is in a contracted configuration where the main portion is contracted such that the first panel region and the second panel region are in closer proximity to each other than in an expanded configuration of the wearable absorbent hygiene article.

In the contracted configuration the main portion may be contracted along a length of the main portion. As expanding the contracted main portion may be an essential step in the application of the wearable absorbent hygiene article, the switch would automatically switch from the OFF state to the ON state. This provides for a reliable switching.

In one embodiment, the first panel region and the second panel region are releasably attachable to each other.

With such a configuration, attaching the first panel region to the second panel region may cause the switch to switch from the OFF state to the ON state. An attachment of one region to another region typically occurs during application of the wearable absorbent hygiene article. Accordingly, with such a configuration, no extra steps are required to start powering the electronics unit. Hence, with such a configuration, the switch would automatically switch from the OFF state to the ON state during the application of the wearable absorbent hygiene article. Moreover, as attaching a first panel region to a second panel region may be an essential step in the application of the wearable absorbent hygiene article, the switch would automatically switch from the OFF state to the ON state. This provides for a reliable switching.

In one embodiment, the switch is configured such that attaching the first panel region and the second panel region to each other switches the switch from the OFF state to the ON state.

In one embodiment, at least one of the first panel region and the second panel region is a side flap or a belt flap.

In one embodiment, the first panel region is a main portion of the wearable absorbent hygiene article. The second panel region is a side portion of the wearable absorbent hygiene article.

Typically, during unpacking/unfolding/application of the wearable absorbent hygiene article, a side portion and a main portion of the wearable absorbent hygiene article experience the greatest degree of relative movement. Accordingly, with such a configuration, the switch may be configured to experience a large degree of change. Hence, with such a configuration, more reliable switching may be possible.

In one embodiment, the wearable absorbent hygiene article is in a folded configuration where the wearable absorbent hygiene article is folded such that the main portion and the side portion at least partially overlap.

With such a configuration, to allow application of the wearable absorbent hygiene article to a wearer, it is ensured that during unfolding, the user must effect a relative movement between the side portion and the main portion of the wearable absorbent hygiene article. Accordingly, this may provide for reliable switching.

In one embodiment, the switch is configured such that a bending and/or stretching and/or compressing of a portion of the wearable absorbent hygiene article switches the switch from the OFF state to the ON state. In a particular embodiment, the portion is a main portion of the wearable absorbent hygiene article.

With such configurations, as a bending and/or stretching and/or compressing of a portion of the wearable absorbent hygiene article typically occurs during unpacking/unfolding/application of the wearable absorbent hygiene article, it may be possible to ensure reliable switching.

In one embodiment, the switch is further configured to switch from the OFF state to the ON state upon detecting a change in at least one physical property experienced by the wearable absorbent hygiene article.

As noted above, as the electronics unit and the power source are included in the wearable absorbent hygiene article, once the wearable absorbent hygiene article is finally put to use, it may be that the power source does not have any stored energy remaining in it.

Ideally, the use of a wearable absorbent hygiene article with an electronics unit should involve the same steps as the use of a typical wearable absorbent hygiene article—any additional steps in using a wearable absorbent hygiene article with an electronics unit may detract from the convenience of using the product.

As noted above, there is a need for an improved convenient-to-use wearable absorbent hygiene article in which an electronics unit may be powered for a longer period of time when the wearable absorbent hygiene article is in use.

With this configuration it is possible to automatically start powering the electronics unit in one of the unpacking/unfolding/applying steps, without requiring any additional steps from the user.

Hence, with such a configuration, it is possible to provide a convenient-to-use wearable absorbent hygiene article in which an electronics unit may be powered for a longer period of time when the wearable absorbent hygiene article is in use.

Typically, during unpacking/unfolding/application of the wearable absorbent hygiene article, at least one physical property experienced by the wearable absorbent hygiene article changes. Accordingly, with the above configuration, the switch may switch from the OFF state to the ON state upon detecting such a change, and, therefore, the switch will switch upon the unpacking/unfolding/applying steps.

In one embodiment, the at least one physical property include temperature and/or atmospheric pressure and/or stress and/or conductivity and/or capacitance.

In one embodiment, the power source constitutes the switch such that the power source is configured to automatically switch from the OFF state to the ON state upon detecting a change in the least one physical property.

The power source constitutes the switch, such that the power source and the switch are a single entity member.

With such a configuration, the complexity of the wearable absorbent hygiene article is reduced.

In one embodiment, the at least one physical property is a physical property experienced by the power source.

In one embodiment, the switch includes at least one sensor. In a particular embodiment, the at least one sensor is a temperature sensor and/or atmospheric pressure sensor and/or a stress sensor and/or conductivity sensor and/or capacitance sensor.

In one embodiment, the switch is further configured to be releasably coupled to an entity and configured such that a decoupling of the switch from the entity switches the switch from the OFF state to the ON state.

The term 'coupled' does not necessarily refer to a physical coupling between the switch and the entity. For example, 'coupling' may refer to a magnetic coupling or an optical coupling.

As noted above, as the electronics unit and the power source are included in the wearable absorbent hygiene article, once the wearable absorbent hygiene article is finally put to use, it may be that the power source does not have any stored energy remaining in it.

Ideally, the use of a wearable absorbent hygiene article with an electronics unit should involve the same steps as the use of a typical wearable absorbent hygiene article—any additional steps in using a wearable absorbent hygiene article with an electronics unit may detract from the convenience of using the product.

As noted above, there is a need for an improved convenient-to-use wearable absorbent hygiene article in which an electronics unit may be powered for a longer period of time when the wearable absorbent hygiene article is in use.

With this configuration, decoupling of the switch of the wearable absorbent hygiene article from an entity may be an essential step in the use of the wearable absorbent hygiene article, and, therefore, the switch would automatically switch from the OFF state to the ON state during use. Hence, it is possible to automatically start powering the electronics unit in one of the unpacking/unfolding/applying steps, without requiring any additional steps from the user.

Hence, with such a configuration it is possible to provide a convenient-to-use wearable absorbent hygiene article in which an electronics unit may be powered by a longer period of time when the wearable absorbent hygiene article is in use.

In one embodiment, the switch is a magnetic switch which is configured to be releasably coupled to a magnetic field of a magnet included in the entity. The magnetic switch is configured such that a movement of the magnet relative to the magnetic switch switches the magnetic switch from the OFF state to the ON state.

With such a configuration, the magnetic switch can be embedded in the wearable absorbent hygiene article such that it does not cause substantial discomfort to the user and cannot be accessed by the user.

In one embodiment, the magnetic switch is a reed switch.

With such a configuration, the magnetic switch is sealed from any substances expelled by the user.

In one embodiment, the switch is configured to be releasably coupled to the entity by a tab included in the entity. The switch is configured such that a decoupling of the switch from the tab switches the switch from the OFF state to the ON state. The switch is a tab switch.

With such a configuration, removal of the tab from the tab switch may allow switching to correspond to a physical change in the wearable absorbent hygiene article such that the user may be alerted that the switching has occurred.

In one embodiment, the switch is configured such that a movement of the wearable absorbent hygiene article relative to the entity switches the switch from the OFF state to the ON state.

According to a second aspect, there is provided a system including the wearable absorbent hygiene article of the first aspect and the entity.

In one embodiment, the entity is a packaging for packaging the wearable absorbent hygiene article.

In one embodiment, the wearable absorbent hygiene article is packaged in the packaging.

In one embodiment, the entity is a wearable absorbent hygiene article or the wearable absorbent hygiene article of the first aspect.

With such configurations, decoupling from the entity (a packaging/another wearable absorbent hygiene article), may be an essential step in the application of the wearable absorbent hygiene article, and, therefore, the switch would automatically switch from the OFF state to the ON state. This provides for a reliable switching.

According to a third aspect, there is provided a method of using a wearable absorbent hygiene article. The wearable absorbent hygiene article includes: a liquid permeable top layer; a back layer; an absorbent member located between the top layer and the back layer; an electronics unit; a power source; and a switch operably coupling the electronics unit to the power source. The switch is configured such that the power source supplies power to the electronics unit when the switch is in an ON state and such that the power source does not supply power to the electronics unit when the switch is in an OFF state. The power source, the switch and at least a portion of the electronics unit are disposed between the top layer and the back layer. The method includes the step of using the wearable absorbent hygiene article. In the using step, the switch is switched from the OFF state to the ON state.

With such a method, it is possible to provide a convenient-to-use wearable absorbent hygiene article with electronic capabilities.

Moreover, using the wearable absorbent hygiene article may include a change in the physical condition of the wearable absorbent hygiene article or a change in a physical condition surrounding the wearable absorbent hygiene article. Therefore, it is possible to provide a convenient method of using a wearable absorbent hygiene article in which an electronics unit may be powered for a longer period of time when the wearable absorbent article is in use.

In one implementation, the step of using the wearable absorbent hygiene article includes the steps of: unpacking the wearable absorbent hygiene article from a packaging when the wearable absorbent hygiene article is packaged in the packaging; and/or unfolding the wearable absorbent hygiene article from a folded configuration of the wearable absorbent hygiene article; and/or applying the wearable absorbent hygiene article. In one of the unpacking, unfolding and applying steps, the switch is switched from the OFF state to the ON state.

Unpacking, unfolding and/or applying are typical steps in the use of conventional wearable absorbent hygiene articles. Accordingly, with such a method, the magnetic switch would automatically switch from the OFF state to the ON state during unpacking/unfolding/application of the wearable absorbent hygiene article, and, therefore, additional steps may not be required by the user to start powering the electronics unit.

In one implementation, the wearable absorbent hygiene article includes a first panel region and a second panel region. In the using step, the switch is switched from the OFF state to the ON state due to a relative movement between the first panel region and the second panel region.

In one implementation, the wearable absorbent hygiene article is the wearable absorbent hygiene article of the first aspect.

In one implementation, in the using step, the switch is switched from the OFF state to the ON state upon detecting a change in at least one physical property experienced by the wearable absorbent hygiene article.

In one implementation, the wearable absorbent hygiene article is the wearable absorbent hygiene article of the first aspect.

In one implementation, the switch is releasably coupled to an entity and further configured such that a decoupling of the switch from the entity switches the switch from the OFF state to the ON state. In the using step, the switch is decoupled from the entity such that the switch is switched from the OFF state to the ON state.

In one implementation, the wearable absorbent hygiene article is the wearable absorbent hygiene article of the first aspect.

BRIEF DESCRIPTION OF THE DRAWINGS

For a better understanding of embodiments of the present invention and to show how the same may be carried into effect, reference will now be made, by way of example only, to the accompanying drawings, in which.

DETAILED DESCRIPTION OF PARTICULAR EMBODIMENTS

Figure 1:
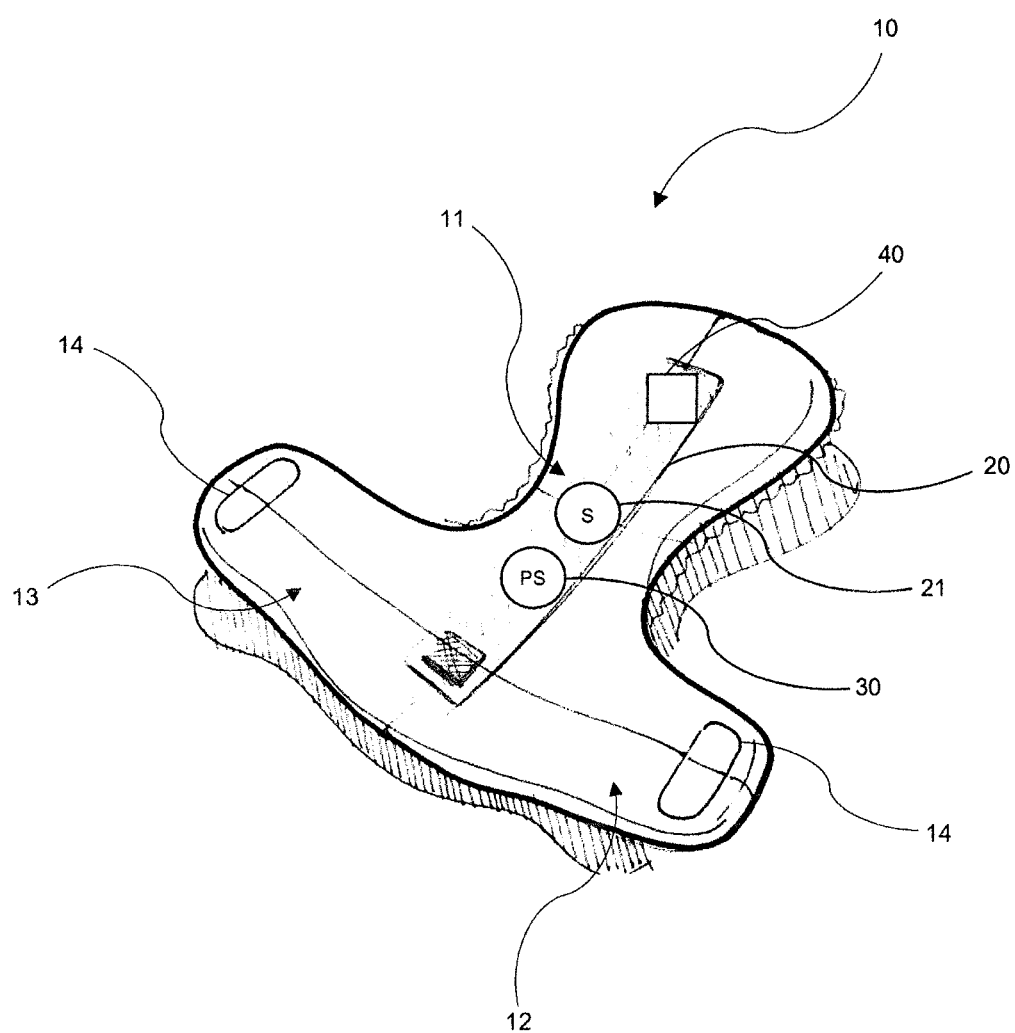
FIG. 1 shows an embodiment of a wearable absorbent hygiene article.

FIG. 1 shows a wearable absorbent hygiene article 10 according to an embodiment.

The wearable absorbent hygiene article 10 has a main portion 11, a first side portion 12, a second side portion 13 and attachment members 14. The main portion 11 is elongate in a first direction. The first side portion 12 and the second side portion 13 extend away from the main portion 11 along a second direction perpendicular to the first direction. The first side portion 12 and the second side portion 13 extend away from the main portion 11 on opposite sides of the main portion 11. An attachment member 14 is disposed on both side portions 12, 13.

The wearable absorbent hygiene article 10 is configured to be worn around the waist of a user by attaching the side portions 12, 13 to the main portion 11 using the attachment members 14.

Figure 2A:
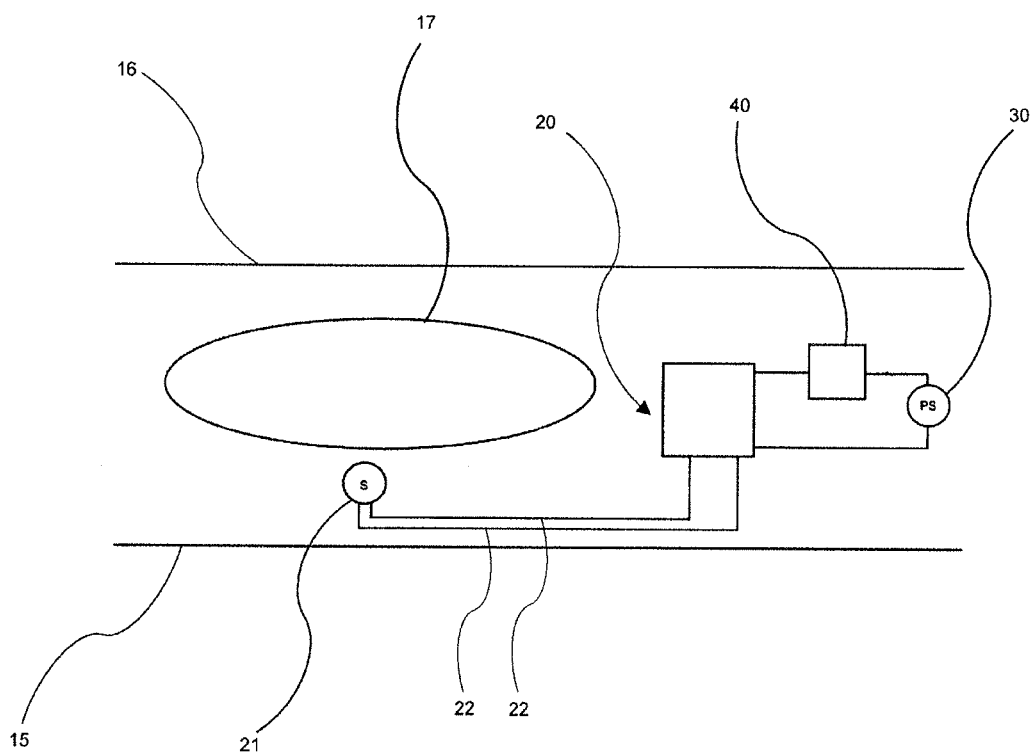
FIGS. 2A to 2C show various arrangements of the electronics unit, sensor, power source and switch of the wearable absorbent hygiene article.
Figure 2B:
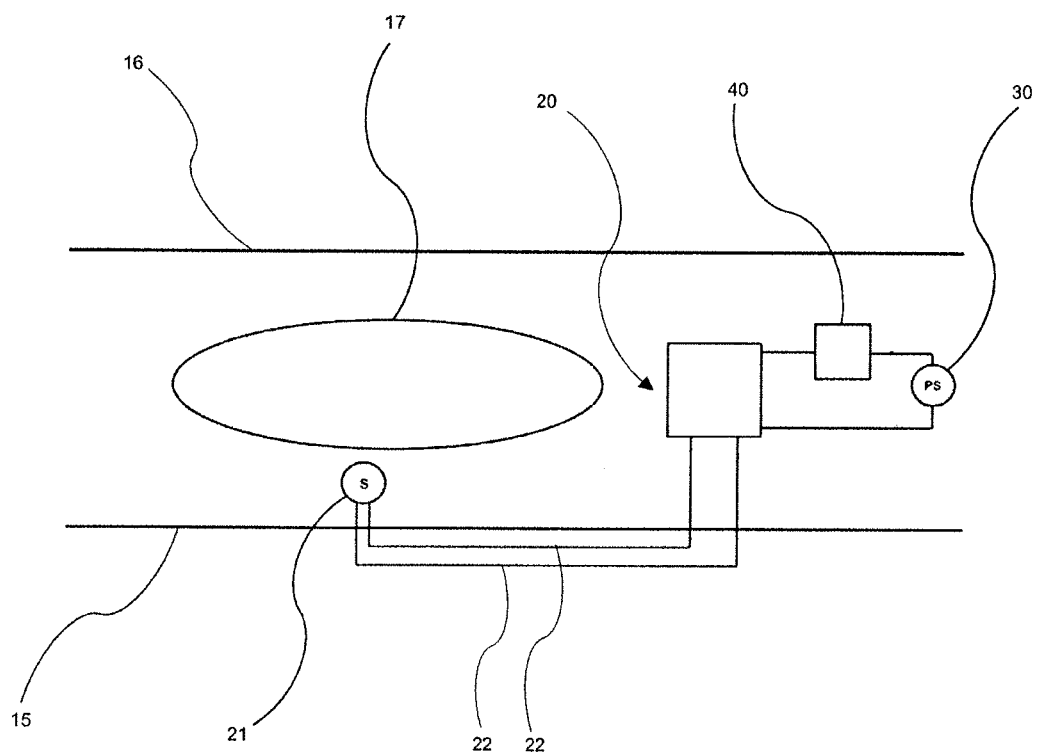
Figure 2C:
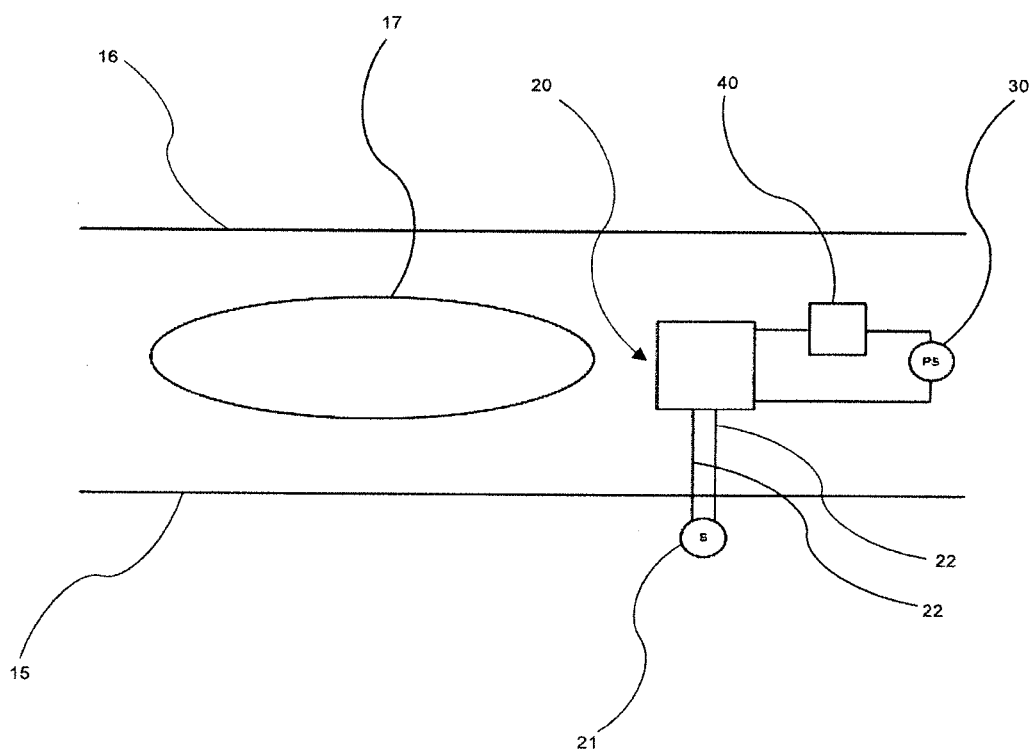

The wearable absorbent hygiene article 10 has a liquid permeable top layer adapted to face the wearer during use and adapted to allow a fluid such as urine or other bodily fluids to pass through; a liquid impermeable back layer adapted to face away from the wearer and adapted to prevent the fluid from passing through; and an absorbent member located between the top layer and the back layer (see FIGS. 2A to 2C).

FIG. 1 shows the wearable absorbent hygiene article 10 in an unfolded configuration. This configuration of the wearable absorbent hygiene article 10 is typical before the application of the wearable absorbent hygiene article 10 to a wearer.

The wearable absorbent hygiene article 10 has an electronics unit 20. The electronics unit 20 is disposed in the main portion 11 of the wearable absorbent hygiene article 10. The electronics unit 20 may be configured to perform various tasks. For example, the electronics unit 20 may include a sensor 21 for sensing a physical environment present in the wearable absorbent hygiene article 10. The sensor may be a wetness sensor, a temperature sensor, a chemical sensor or a biological sensor. The electronics unit 20 may be configured in a variety of ways to perform a variety of different tasks.

The electronics unit 20 may further include a transmitter for transmitting information relating to the physical environment present in the wearable absorbent hygiene article 10 or other relevant information. The electronics unit 20 may further include a receiver for receiving information such as instructions.

The wearable absorbent hygiene article 10 includes a power source 30. In the wearable absorbent hygiene article 10 shown in FIG. 1, the power source 30 is provided in the main portion 11 of the wearable absorbent hygiene article 10. As shown, the power source 30 is disposed on the electronics unit 20. The power source 30 may hold an energy store in the form of electrical energy and/or a chemical energy. The power source 30 may be any type of power source such as a cell, battery and/or a capacitor. For example, the power source 30 may be a flexible paper cell/battery such as those provided by Blue Spark Technologies (OH, US), Enfucell Oy (FI), GS Nanotech (KR) or Cymbet (MN, US).

The wearable absorbent hygiene article 10 has a switch 40. In the wearable absorbent hygiene article 10 shown in FIG. 1, the switch 40 is provided in the main portion 11 of the wearable absorbent hygiene article 10. As shown, the switch 40 is disposed on the electronics unit 20.

The switch 40 operably couples the electronics unit 20 to the power source 30. The switch 40 has an ON state and an OFF state. The switch 40 is configured such that the power source 30 supplies power to the electronics unit 20 when the switch 40 is in an ON state. The switch 40 is configured such that the power source 30 does not supply power to the electronics unit 20 when the switch 40 is in an OFF state. When the switch 40 is in the OFF state, a complete circuit between the power source 30 and the electronics unit 20 is not present. In such a state, the electronics unit 20 is not powered by the power source 30, and, therefore, the power source 30 largely maintains its energy store.

Further details of the various embodiments of the switch 40 will be described below.

The power source 30, the switch 40 and at least a portion of the electronics unit 20 are disposed between the top layer and the back layer. FIGS. 2A, 2B and 2C show various arrangements of the electronics unit 20 including sensor 21, power source 30 and switch 40 of the wearable absorbent hygiene article 10. In each of these embodiments, the wearable absorbent hygiene article 10 has a top layer 16 adapted to face the wearer during use, a back layer 15 opposite to the top layer 16, and an absorbent member 17 located between the back layer 15 and the top layer 16. FIGS. 2A, 2B and 2C each show a cross-section of a portion of the wearable absorbent hygiene article 10. For example, these cross-sections may be cross-sections of the main portion 11 of the wearable absorbent hygiene article 10.

FIG. 2A shows an embodiment in which the power source 30, the switch 40 and the whole of the electronics unit 20, including the sensor 21, are disposed between the back layer 15 and the top layer 16.

FIG. 2B shows an alternate embodiment in which the leads 22 of the electronics unit 20 are not disposed between the back layer 15 and the top layer 16. Accordingly, only a portion of the electronics unit 20 is disposed between the top layer 16 and the back layer 15.

FIG. 2C shows another embodiment in which the sensor 21 of the electronics unit 20 is not disposed between the back layer 15 and the top layer 16. Accordingly, only a portion of the electronics unit 20 is disposed between the back layer 15 and the top layer 16.

Figure 3:
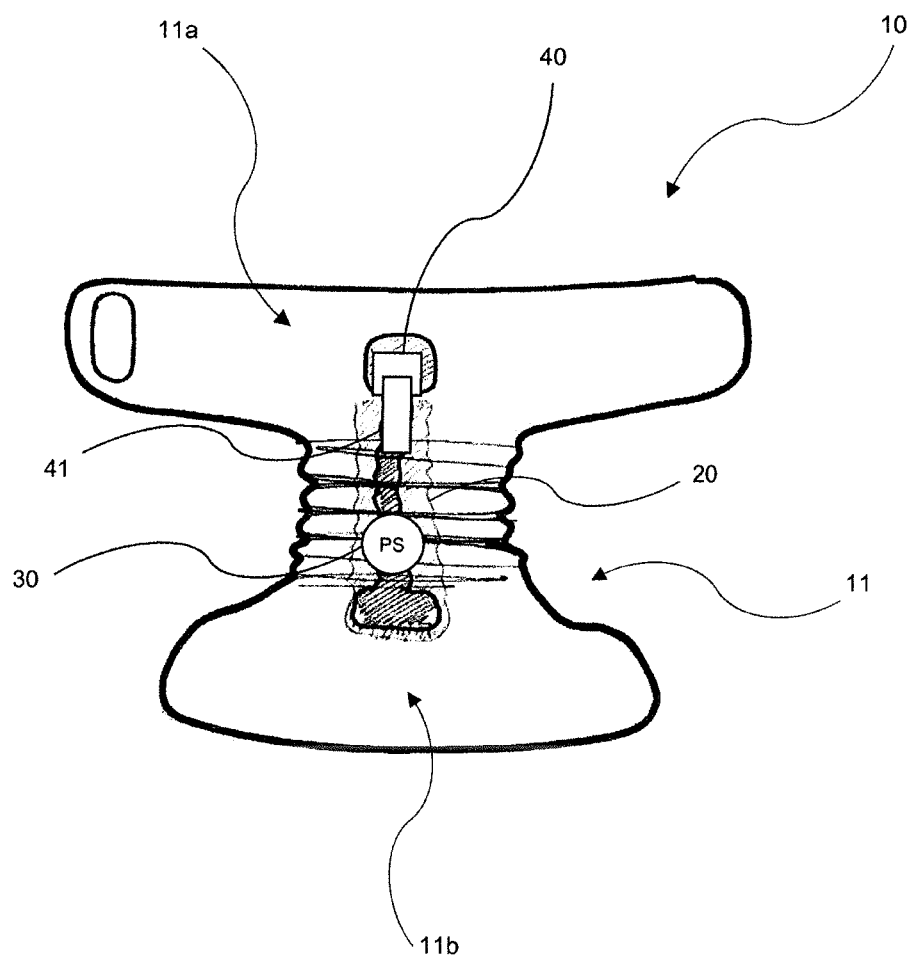
FIG. 3 shows an embodiment of the wearable absorbent hygiene article in a contracted configuration.

FIG. 3 shows an embodiment of the wearable absorbent hygiene article 10. The wearable absorbent hygiene article 10 of this embodiment is generally similar to the wearable absorbent hygiene article 10 of the previous embodiment. Accordingly, only certain differences of this embodiment will be described below.

In this embodiment, the switch is a tab switch 40 in which disconnection of a tab 41 results in the tab switch 40 being switched from the OFF state to the ON state. The tab switch 40 has an intact state which corresponds to an OFF state of the tab switch 40. The tab switch 40 has a broken state which corresponds to an ON state of the tab switch 40. In the broken state, the tab 41 has been removed from the tab switch 40.

FIG. 3 shows the wearable absorbent hygiene article 10 in a contracted configuration. In this contracted configuration, the main portion 11 of the wearable absorbent hygiene article 10 is contracted along the first direction. In this configuration, the tab switch 40 is in an intact state which corresponds to an OFF state of the tab switch 40.

Figure 4:
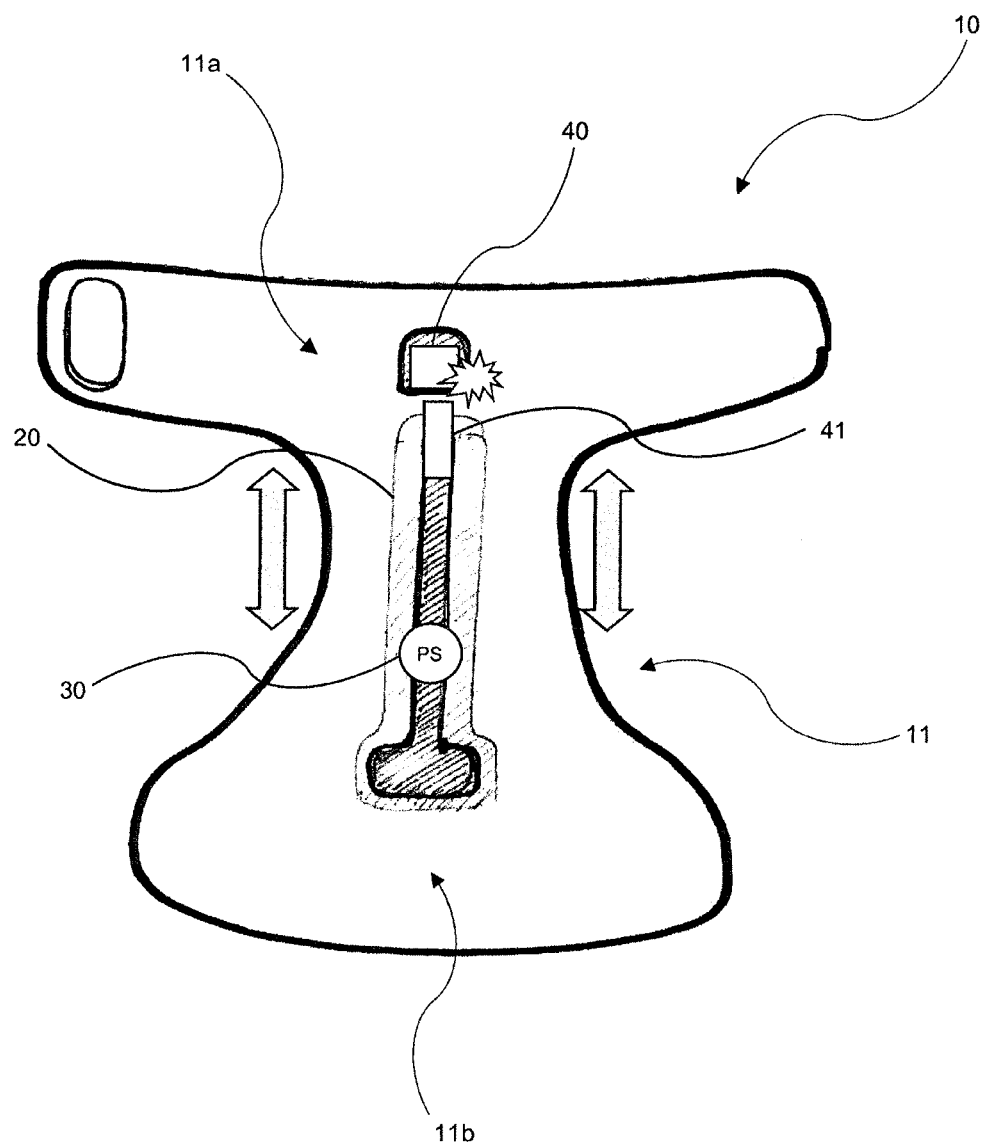
FIG. 4 shows the wearable absorbent hygiene article shown in FIG. 3 in an expanded configuration.

FIG. 4 shows the wearable absorbent hygiene article 10 of this embodiment in an expanded configuration. This configuration may result from a user expanding the main portion 11 along the first direction of the wearable absorbent hygiene article 10 from the configuration shown in FIG. 3. In this configuration, the front main panel region 11a of the main portion 11 has been moved away from the back main panel region 11b of the main portion 11. In doing so, the tab switch 40 has been transitioned to the broken state. The tab switch 40 is configured such that transitioning from the intact state to the broken state results in the tab switch 40 being switched from the OFF state to the ON state. Accordingly, the tab switch 40 is configured to switch from the OFF state to the ON state when the user expands the main portion 11 of the wearable absorbent hygiene article 10 from the contracted configuration shown in FIG. 3 to the expanded configuration shown in FIG. 4.

A method of using the wearable absorbent hygiene article 10 of this embodiment will now be described with respect to FIGS. 3 and 4. Generally, using the wearable absorbent hygiene article 10 may include a change in the physical condition of the wearable absorbent hygiene article 10 or a change in the physical conditions surrounding the wearable absorbent hygiene article 10. In this embodiment, using the wearable absorbent hygiene article 10 includes expanding the wearable absorbent hygiene article 10 from the contracted configuration shown in FIG. 3 to the expanded configuration shown in FIG. 4. Before this expanding step, the tab switch 40 is in an intact state in which the tab switch 40 is in the OFF state. During the expanding step, the tab switch 40 is transitioned to the broken state and switched from the OFF state to the ON state such that the electronics unit 20 is powered by the power source 30. Once the wearable absorbent hygiene article 10 is expanded it may then be applied to the waist of the wearer.

Figure 5:
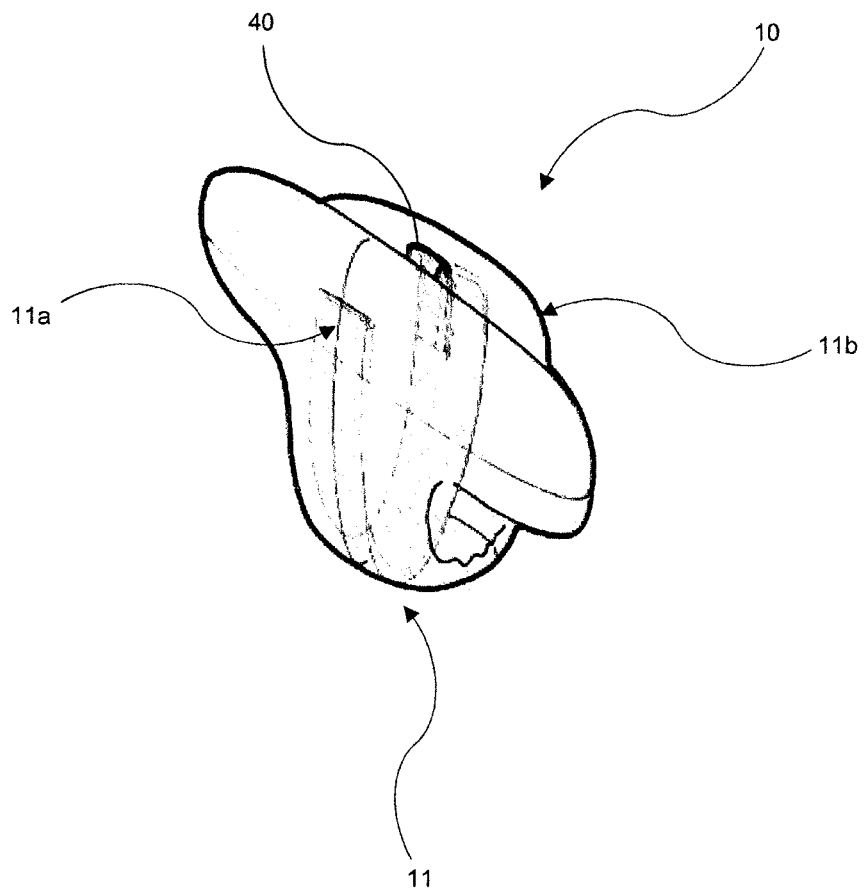
FIG. 5 shows another embodiment of the wearable absorbent hygiene article in a folded configuration.

FIG. 5 shows another embodiment of the wearable absorbent hygiene article 10. The wearable absorbent hygiene article 10 of this embodiment is generally similar to the previous embodiment. Accordingly, only certain differences of this embodiment will be described below.

FIG. 5 shows a wearable absorbent hygiene article 10 in a folded configuration.

In this embodiment, the switch is a tab switch 40, as described above.

In this folded configuration, the main portion 11 is folded such that the front main panel region 11a of the main portion 11 overlaps with the back main panel region 11b of the main portion 11. In this configuration, the tab switch 40 is in an intact state which corresponds to an OFF state of the tab switch 40.

Figure 6:
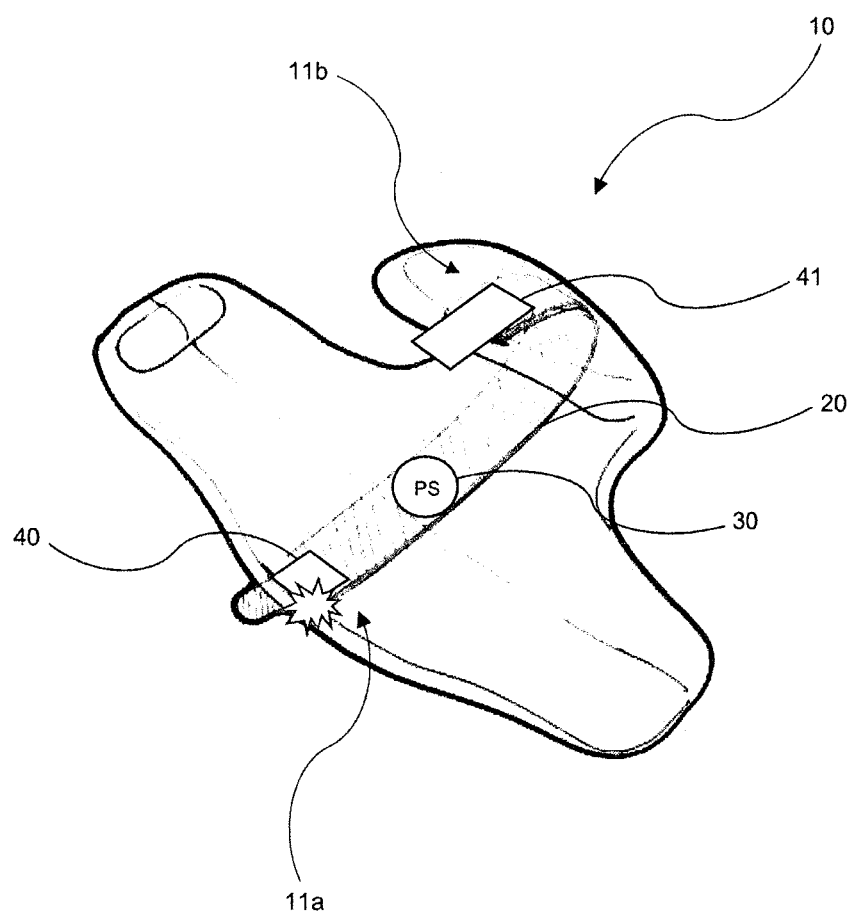
FIG. 6 shows the wearable absorbent hygiene article shown in FIG. 5 in an unfolded configuration.

FIG. 6 shows the wearable absorbent hygiene article 10 of this embodiment in an unfolded configuration. This unfolded configuration may result from a user unfolding the wearable absorbent hygiene article 10 from the configuration shown in FIG. 5. Specifically, in FIG. 6, the front main panel region 11a and the back main panel region 11b have been separated from one another such that the main portion 11 has been unfolded. In doing so, the user has switched the tab switch 40 from the intact state to the broken state in which the tab 41 has been removed from the tab switch 40. In this broken state, the tab switch 40 is in the ON state. Accordingly, the tab switch 40 is configured to switch from the OFF state to the ON state when the user unfolds the main portion 11 of the wearable absorbent hygiene article 10 from the folded configuration shown in FIG. 5 to the unfolded configuration shown in FIG. 6.

A method of using the wearable absorbent hygiene article 10 of this embodiment will now be described with respect to FIGS. 5 and 6. Using the wearable absorbent hygiene article 10 of this embodiment includes unfolding the wearable absorbent hygiene article 10 from the folded configuration shown in FIG. 5 to the unfolded configuration shown in FIG. 6. Before this unfolding step, the tab switch 40 is in the OFF state. During the unfolding step, the tab switch 40 is switched from the OFF state to the ON state such that the electronics unit 20 is powered by the power source 30. Once the wearable absorbent hygiene article 10 is unfolded as shown in FIG. 6, it may then be applied to the waist of the wearer.

Figure 7:
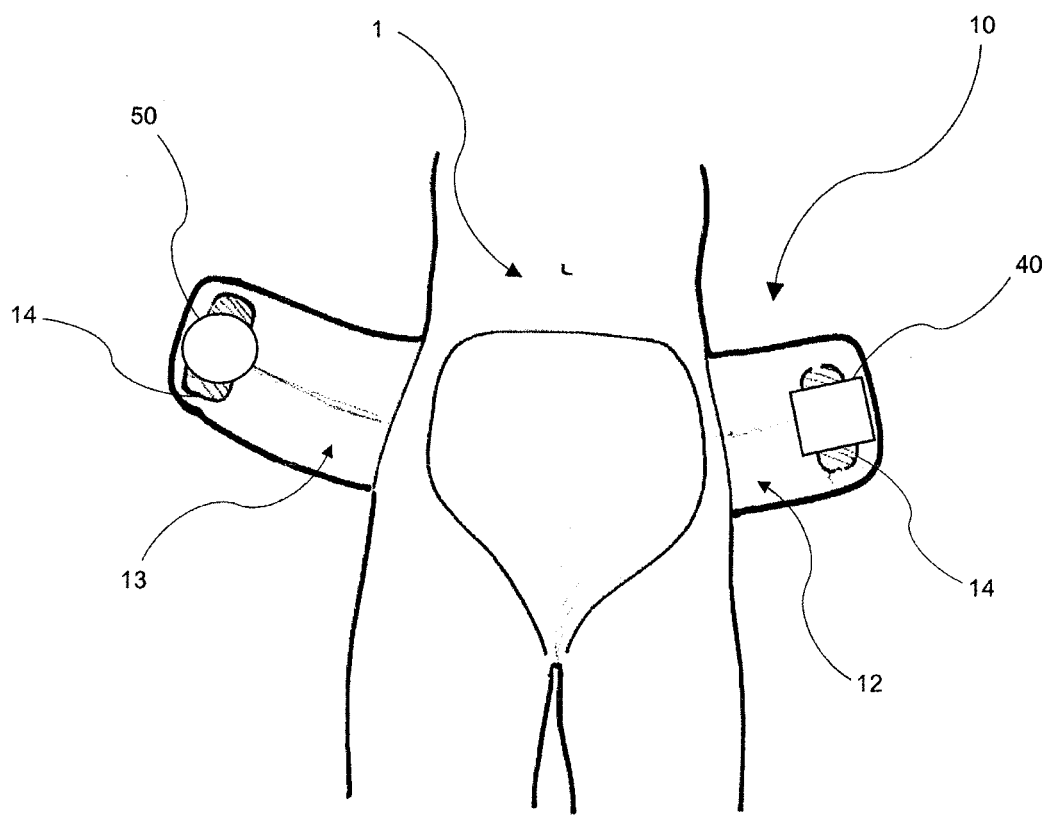
FIG. 7 shows another embodiment of the wearable absorbent hygiene article in an open configuration.

FIG. 7 shows another embodiment of the wearable absorbent hygiene article 10. The wearable absorbent hygiene article 10 of this embodiment is generally similar to the wearable absorbent hygiene article 10 of the previous embodiments. Accordingly, only certain differences of this embodiment will be described below.

In this embodiment, the switch 40 is a magnetic switch. The wearable absorbent hygiene article 10 of this embodiment also includes a magnet 50.

Throughout this disclosure, the term 'magnet' refers to any device/material which creates a magnetic field.

Throughout this disclosure, the term 'magnetic switch' refers to any switch which is configured to be in a particular state depending on the magnetic field experienced by the switch. The magnetic switch may switch between states when the magnetic field experienced by the magnetic switch changes. The particular change in magnetic field required to switch the magnetic switch between states may be predetermined depending on the particular configuration of the magnetic switch.

FIG. 7 shows the wearable absorbent hygiene article 10 in an open configuration before being applied to the waist of a user 1.

The first side panel portion 12 has the magnetic switch 40. The second side panel portion 13 has the magnet 50. The first side panel portion 12 and the second side panel portion 13 each have an attachment member 14. In the open configuration shown, the first side panel portion 12 and the second side panel portion 13 are separated from one another. As the magnetic switch 40 and the magnet 50 are disposed relatively distally from one another, in this configuration, the magnetic switch 40 experiences a first magnetic field.

Figure 8:
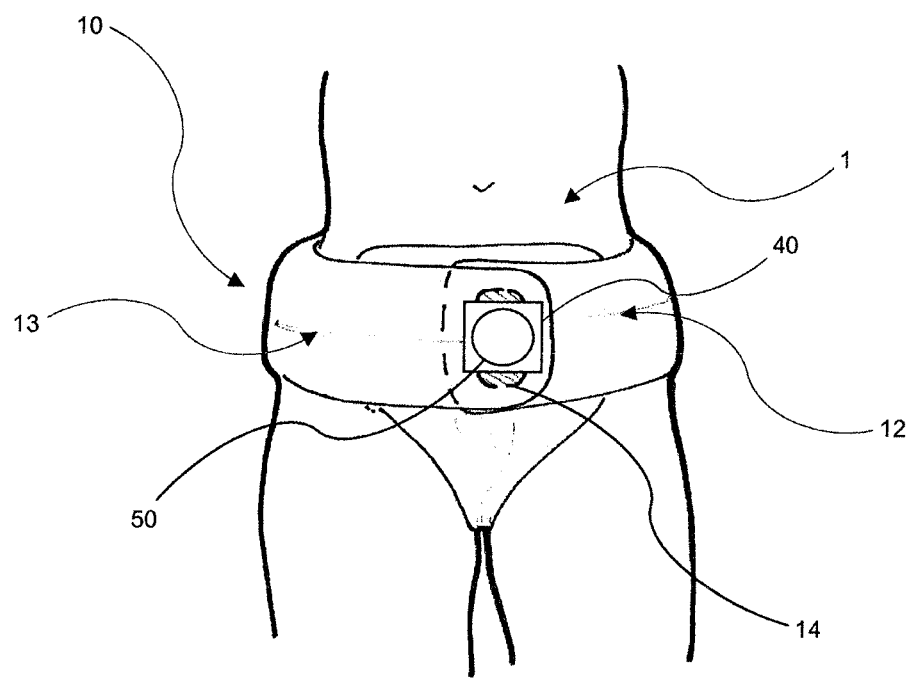
FIG. 8 shows the wearable absorbent hygiene article shown in FIG. 7 in a closed configuration.

FIG. 8 shows the wearable absorbent hygiene article 10 of the third embodiment in a closed configuration in which the wearable absorbent hygiene article 10 has been applied to the waist of a user 1. This configuration may result from a user bringing the first side panel portion 12 and the second side panel portion 13 into contact with one another from the configuration shown in FIG. 7. In doing so, the user may have attached the attachment members 14 of the first side panel portion 12 and the second side panel portion 13 to each other, thereby securing the wearable absorbent hygiene article 10 to the waist of the user 1. Bringing together the first side panel portion 12 and the second side panel portion 13 results in the magnet 50 being moved towards the magnetic switch 40. As shown in FIG. 8, in the closed configuration, the magnetic switch 40 and the magnet 50 overlap with one another. In this configuration, the magnetic switch 40 experiences a second magnetic field. Specifically, the magnetic field experienced by the magnetic switch 40 in the closed configuration shown in FIG. 8 is larger than the magnetic field experienced by the magnetic switch 40 in the open configuration shown in FIG. 7. The magnetic switch 40 may be configured such that this change in magnetic field experienced by the magnetic switch 40 switches the magnetic switch 40 from the OFF state to the ON state. Accordingly, the magnetic switch 40 is configured to switch from the OFF state to the ON state when the user brings the first side panel portion 12 and the second side panel portion 13 together when applying the wearable absorbent hygiene article 10 from the open configuration shown in FIG. 7 to the closed configuration shown in FIG. 8.

A method of using the wearable absorbent hygiene article 10 of the third embodiment will now be described with respect to FIGS. 7 and 8. Using the wearable absorbent hygiene article 10 of this embodiment includes applying the wearable absorbent hygiene article 10 to a user 1. Applying the wearable absorbent hygiene article 10 includes bringing the first side panel portion 12 and the second side panel portion 13 into contact with each other such that the attachment members 14 on each of the side portions 12, 13 attach to each other. This can be effected from the open configuration shown in FIG. 7 so as to result in the closed configuration shown in FIG. 8. Before this applying step, the magnetic switch 40 is in the OFF state. During the applying step, the magnetic switch 40 is switched from the OFF state to the ON state such that the electronics unit 20 (not shown in FIGS. 7 and 8) is powered by the power source 30 (not shown in FIGS. 7 and 8).

Figure 9:
FIG. 9 shows another embodiment of the wearable absorbent hygiene article.

FIG. 9 shows another embodiment of the wearable absorbent hygiene article 10. This embodiment is generally similar to the wearable absorbent hygiene article 10 of the previous embodiments. Accordingly, only certain differences of this embodiment will be described below.

The switch 40 of the wearable absorbent hygiene article 10 is configured to switch from the OFF state to the ON state upon detecting a change in at least one physical property experienced by the wearable absorbent hygiene article 10.

In the embodiment shown in FIG. 9, the switch 40 has a stress sensor which is configured to switch from the OFF state to the ON state when the user 1 sits on the wearable absorbent hygiene article 10 such that the stress sensed by the stress sensor increases above a predetermined threshold.

A method of using the wearable absorbent hygiene article 10 of this embodiment will now be described with respect to FIG. 9. Using the wearable absorbent hygiene article 10 of this embodiment includes wearing the wearable absorbent hygiene article 10. Typically, during wearing of the wearable absorbent hygiene article 10, the user 1 may sit down such that a portion of the wearable absorbent hygiene article 10 is compressed. Before this wearing step, the switch 40 is in the OFF state. During this wearing step, the switch 40 is switched from the OFF state to the ON state such that the electronics unit 20 (not shown in FIG. 9) is powered by the power source 30 (not shown in FIG. 9).

Figure 10:
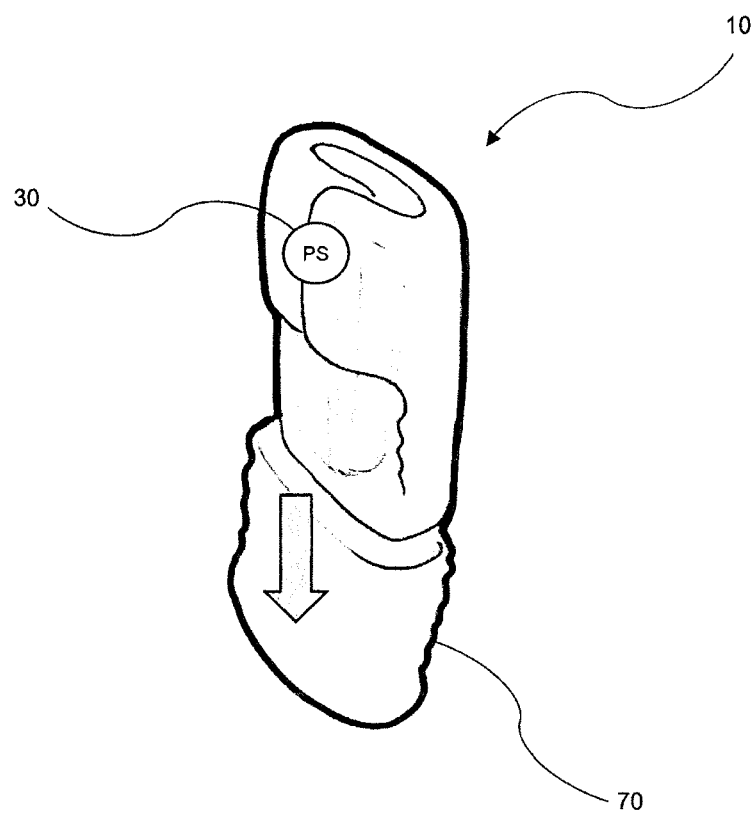
FIG. 10 shows another embodiment of the wearable absorbent hygiene article.

FIG. 10 shows another embodiment of the wearable absorbent hygiene article 10. This embodiment is generally similar to the wearable absorbent hygiene article 10 of the previous embodiments. Accordingly, only certain differences of this embodiment will be described below.

In the embodiment shown in FIG. 10, the power source 30 constitutes the switch such that the power source 30 is configured to switch from the OFF state to the ON state upon experiencing a change in at least one physical property.

Specifically, the power source 30 and the switch are a single entity/member.

FIG. 10 shows a configuration in which the wearable absorbent hygiene article 10 has been removed from a packaging bag 70. Previous to this configuration, the wearable absorbent hygiene article 10 is contained in a vacuum in the packaging bag 70. Accordingly, the wearable absorbent hygiene article 10 and specifically the power source 30 experience a very low/zero pressure.

In the configuration shown in FIG. 10, the wearable absorbent hygiene article 10 has been removed from the packaging bag 70, and, therefore, the wearable absorbent hygiene article 10 and specifically the power source 30 experience a non-zero pressure (atmospheric pressure).

The power source 30 is configured such that this change in pressure results in the power source 30 being switched from the OFF state to the ON state. For example, the power source 30 may be an zinc air battery.

A method of using the wearable absorbent hygiene article 10 of this embodiment will now be described with respect to FIG. 10. Using the wearable absorbent hygiene article 10 of this embodiment includes unpacking the wearable absorbent hygiene article 10 from the packaging bag 70. Unpacking the wearable absorbent hygiene article 10 from the packaging bag 70 includes removing the wearable absorbent hygiene article 10 from the packaging bag 70, as shown by the arrow in FIG. 10. Before this unpacking step, the power source 30 is in the OFF state. During the unpacking step, the power source 30 is switched from the OFF state to the ON state such that the electronics unit 20 (not shown in FIG. 10) is powered by the power source 30 (not shown in FIG. 10). Once the wearable absorbent hygiene article 10 is unpackaged, it may then be applied to the waist of the wearer.

Figure 11:
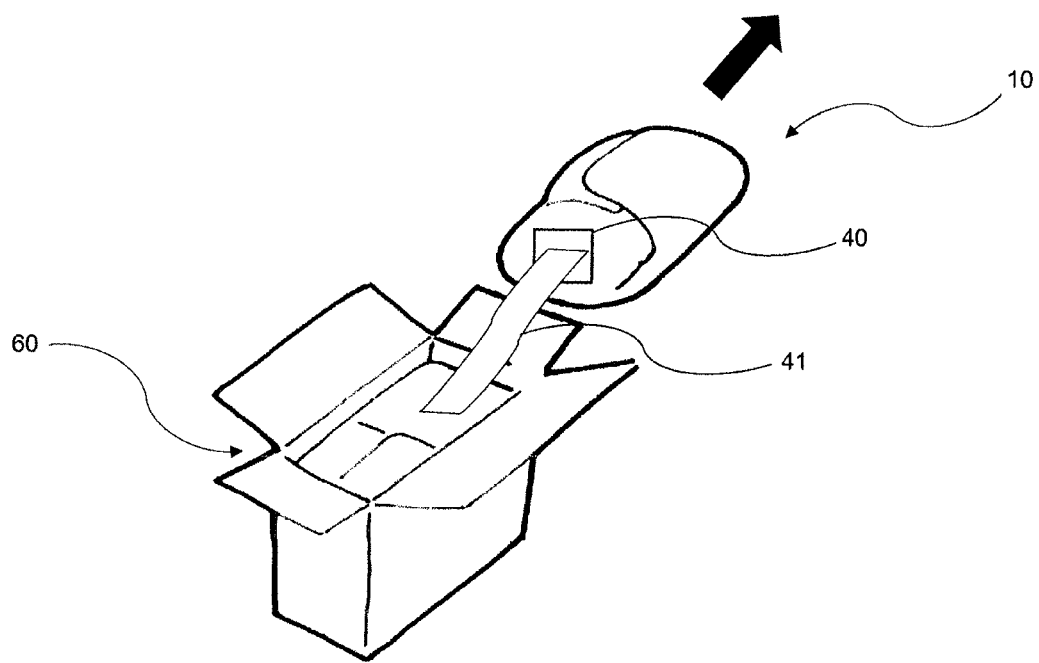
FIG. 11 shows another embodiment of the wearable absorbent hygiene article.

FIG. 11 shows another embodiment of the wearable absorbent hygiene article 10. The wearable absorbent hygiene article 10 of this embodiment is generally similar to the wearable absorbent hygiene article 10 of the previous embodiments. Accordingly, only certain differences of this embodiment will be described below.

In this embodiment, the switch is a tab switch 40, as described above.

The switch 40 of the wearable absorbent hygiene article 10 is releasably coupled to the packaging box 60 by the tab 41 and configured such that a decoupling of the switch 40 from the packaging box 60 switches the switch 40 from the OFF state to the ON state. The tab 41 is fixed to the packaging box 60.

FIG. 11 shows a configuration in which the tab switch 40 of the wearable absorbent hygiene article 10 is coupled to the packaging box 60 by tab 41. FIG. 11 shows a state in which the wearable absorbent hygiene article 10 is being unpackaged from the packaging box 60 by movement in the direction shown by the arrow. In this state, the tab switch 40 is in the intact state in which the switch 40 is in the OFF state.

Figure 12:
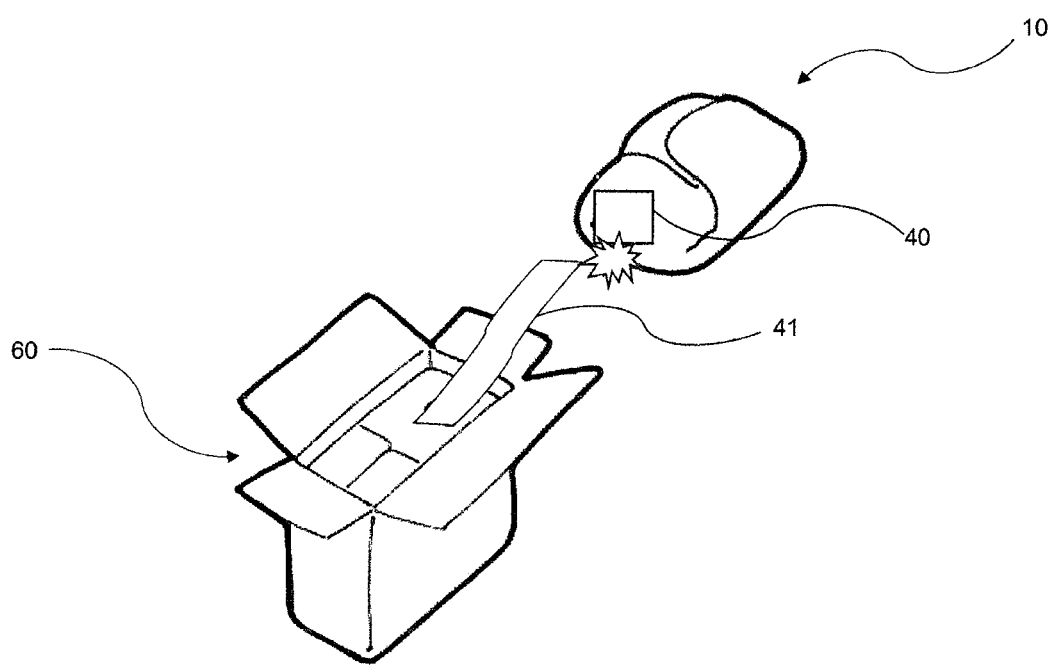
FIG. 12 shows the wearable absorbent hygiene article shown in FIG. 11 fully unpackaged from the packaging box.

FIG. 12 shows the wearable absorbent hygiene article 10 fully unpackaged from the packaging box 60. The switch 40 is in the broken state in which the switch 40 is in the ON state.

A method of using the wearable absorbent hygiene article 10 of this embodiment will now be described with respect to FIGS. 11 and 12. Using the wearable absorbent hygiene article 10 of this embodiment includes unpacking the wearable absorbent hygiene article 10 from the packaging box 60. Unpacking the wearable absorbent hygiene article 10 from the packaging box 60 includes moving the wearable absorbent hygiene article 10 away from the packaging box 60, as shown by the arrow in FIG. 11. Before this unpacking step, the switch 40 is in the OFF state. During the unpacking step, the switch is switched from the OFF state to the ON state such that the electronics unit 20 (not shown in FIGS. 11 and 12) is powered by the power source 30 (not shown in FIGS. 11 and 12). Once the wearable absorbent hygiene article is unpackaged, it may then be applied to the waist of a wearer.

Figure 13:
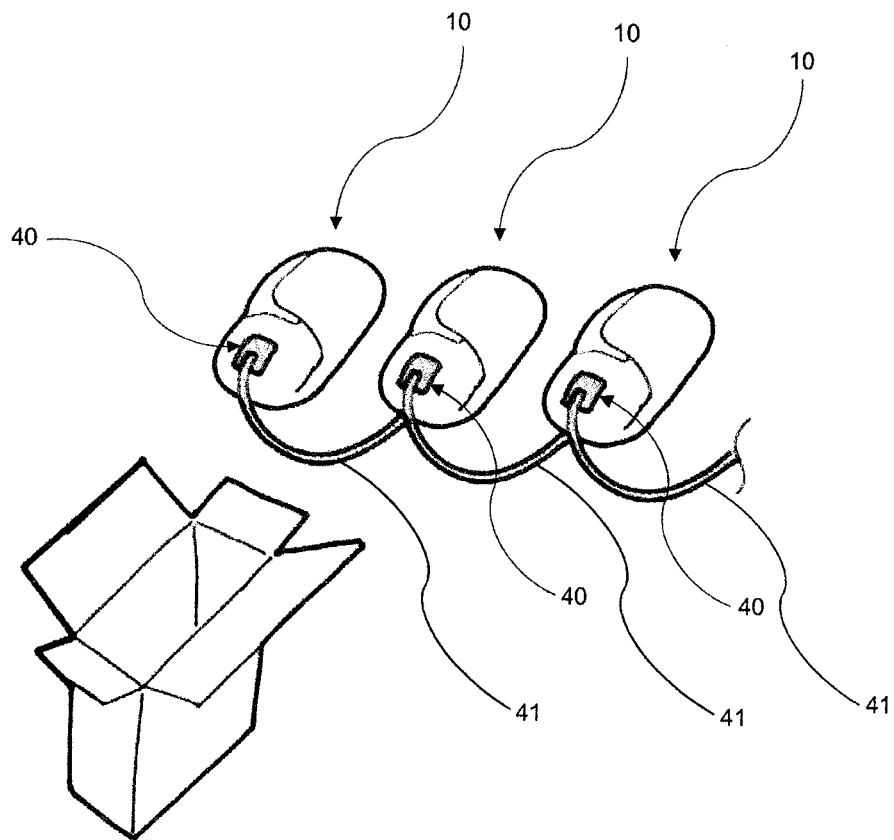
FIG. 13 shows another embodiment of the wearable absorbent hygiene article.

FIG. 13 shows another embodiment of the wearable absorbent hygiene article 10. As shown in FIG. 13, there are three wearable absorbent hygiene articles 10.

In this embodiment, the switch is a tab switch 40, as described above.

Each of the wearable absorbent hygiene articles 10 have a tab switch 40 coupled to another wearable absorbent hygiene article 10 by tabs 41. This embodiment is similar to the embodiment described with respect to FIGS. 11 and 12. As a tab switch 40 of one wearable absorbent hygiene article 10 is transitioned to a broken state by movement of the wearable absorbent hygiene article 10 away from the other wearable absorbent hygiene article 10, the switch 40 is switched from the OFF state to the ON state.

Although the above explanation is considered to fully clarify how embodiments of the present invention may straightforwardly be put into effect by those skilled in the art, they are to be regarded as purely exemplary.

In particular, there are a number of variations which are possible, as may be appreciated by those skilled in the art.

For example, the power source 30, the switch 40 and at least a portion of the electronics unit 20 may be disposed at various locations within the wearable absorbent hygiene article 10 as long as they are disposed between the top layer 16 and the back layer 15.

Furthermore, the switch 40 may be any type of switch which may be switched from the OFF state to the ON state by any means. For example, the switch 40 may be a magnetic switch, a tab switch or an optical switch. Moreover, the switch 40 may be disposed in various locations within the wearable absorbent hygiene article 10.

Furthermore, the switch may be configured to switch from the OFF state to the ON state upon detecting a change in at least one physical property where the physical property is room temperature, body temperature, body weight, insulation and/or capacitance.

In an alternative embodiment to the embodiments shown in FIGS. 11 to 13, the wearable absorbent hygiene article 10 may be coupled to a packaging bag in which, prior to use, it may be contained in.

All of the above are fully within the scope of the present invention, and are considered to form the basis for alternative embodiments in which one or more combinations of the above-described features are applied, without limitation to the specific combinations disclosed above.

In light of this, there will be many alternatives which implement the teaching of the present invention. It is expected that one skilled in the art will be able to modify and adapt the above disclosure to suit its own circumstances and requirements within the scope of the present invention, while retaining some or all technical effects of the same, either disclosed or derivable from the above, in light of his general knowledge in this art. All such equivalents, modifications or adaptations fall within the scope of the invention hereby defined by the claims.

The invention claimed is:

1. A wearable absorbent hygiene article comprising:
a liquid permeable top layer adapted to face the wearer during use;
a back layer opposite to the top layer;
an absorbent member located between the top layer and the back layer;
a first panel region;
a second panel region;
an electronics unit;
a power source; and
a switch operably coupling the electronics unit to the power source, the switch being configured such that the power source supplies power to the electronics unit when the switch is in an ON state and such that the power source does not supply power to the electronics unit when the switch is in an OFF state, wherein the switch is further configured such that a movement of the first panel region relative to the second panel region switches the switch from the OFF state to the ON state,
wherein the power source, the switch, and at least a portion of the electronics unit are disposed between the top layer and the back layer.

2. The wearable absorbent hygiene article of claim 1, wherein the electronics unit comprises at least one sensor for sensing a physical environment present in the wearable absorbent hygiene article.

3. The wearable absorbent hygiene article of claim 1, wherein the electronics unit comprises a transmitter, a receiver, or both.

4. The wearable absorbent hygiene article of claim 1, wherein the power source is a cell.

5. The wearable absorbent hygiene article of claim 1, wherein, in a folded configuration, the wearable absorbent hygiene article is folded such that the first panel region and the second panel region at least partially overlap.

6. The wearable absorbent hygiene article of claim 1, further comprising a main portion, wherein the first panel region is one region of the main portion and the second panel region is another region of the main portion.

7. The wearable absorbent hygiene article of claim 6, wherein, in a contracted configuration, the main portion is contracted such that the first panel region and the second panel region are in closer proximity to each other than in an expanded configuration of the wearable absorbent hygiene article.

8. The wearable absorbent hygiene article of claim 1, wherein the first panel region and the second panel region are releasably attachable to each other.

9. The wearable absorbent hygiene article of claim 8, wherein the switch is configured such that attaching the first panel region and the second panel region to each other switches the switch from the OFF state to the ON state.

10. The wearable absorbent hygiene article of claim 8, wherein at least one of the first panel region and the second panel region is a side flap or a belt flap.

11. The wearable absorbent hygiene article of claim 1, wherein the first panel region is a main portion of the wearable absorbent hygiene article and the second panel region is a side portion of the wearable absorbent hygiene article.

12. The wearable absorbent hygiene article of claim 11, wherein, in a folded configuration, the wearable absorbent hygiene article is folded such that the main portion and the side portion at least partially overlap.

13. The wearable absorbent hygiene article of claim 1, wherein the switch is a magnetic switch being configured such that a bending, stretching, or compressing of a portion of the wearable absorbent hygiene article switches the switch from the OFF state to the ON state.

14. A wearable absorbent hygiene article comprising:
   a liquid permeable top layer adapted to face the wearer during use;
   a back layer opposite to the top layer;
   an absorbent member located between the top layer and the back layer;
   an electronics unit;
   a power source; and
   a switch operably coupling the electronics unit to the power source, the switch being configured such that the power source supplies power to the electronics unit when the switch is in an ON state and such that the power source does not supply power to the electronics unit when the switch is in an OFF state, wherein the switch is further configured to switch from the OFF state to the ON state upon detecting a change experienced by the wearable absorbent hygiene article in at least one physical property selected from the group consisting of temperature, atmospheric pressure, stress, and capacitance,
   wherein the power source, the switch, and at least a portion of the electronics unit are disposed between the top layer and the back layer.

15. The wearable absorbent hygiene article of claim 14, wherein the power source constitutes the switch such that the power source is configured to automatically switch from the OFF state to the ON state upon detecting a change in the least one physical property.

16. The wearable absorbent hygiene article of claim 15, wherein the at least one physical property is a physical property experienced by the power source.

17. The wearable absorbent hygiene article of claim 14, wherein the switch comprises at least one sensor.

18. A wearable absorbent hygiene article comprising:
   a liquid permeable top layer adapted to face the wearer during use;
   a back layer opposite to the top layer;
   an absorbent member located between the top layer and the back layer;
   an electronics unit;
   a power source; and
   a switch operably coupling the electronics unit to the power source, the switch being configured such that the power source supplies power to the electronics unit when the switch is in an ON state and such that the power source does not supply power to the electronics unit when the switch is in an OFF state, wherein the switch is further configured to be releasably coupled to an entity and configured such that a decoupling of the switch from the entity switches the switch from the OFF state to the ON state,
   wherein the power source, the switch, and at least a portion of the electronics unit are disposed between the top layer and the back layer.

19. The wearable absorbent hygiene article of claim 18, wherein the switch is a magnetic switch which is configured to be releasably coupled to a magnetic field of a magnet included in the entity, and wherein the magnetic switch is configured such that a movement of the magnet relative to the magnetic switch switches the magnetic switch from the OFF state to the ON state.

20. The wearable absorbent hygiene article of claim 18, wherein the switch is configured to be releasably coupled to the entity by a tab included in the entity, and wherein the switch is configured such that a decoupling of the switch from the tab switches the switch from the OFF state to the ON state.

21. The wearable absorbent hygiene article of claim 18, wherein the switch is configured such that a movement of the wearable absorbent hygiene article relative to the entity switches the switch from the OFF state to the ON state.

\* \* \* \* \*